(12) United States Patent
Chornenky et al.

(10) Patent No.: US 7,086,577 B2
(45) Date of Patent: Aug. 8, 2006

(54) METHOD OF MANUFACTURING A MINIATURE X-RAY DEVICE

(75) Inventors: Victor I Chornenky, Santa Rosa, CA (US); Eunsung Park, Arden Hills, MN (US); Graham S. Kerslick, Ithaca, NY (US); Ali Jaafar, Eden Prairie, MN (US); Mark Gailloux, Eden Prairie, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 511 days.

(21) Appl. No.: 10/358,265

(22) Filed: Feb. 5, 2003

(65) Prior Publication Data

US 2003/0133541 A1 Jul. 17, 2003

Related U.S. Application Data

(62) Division of application No. 09/760,815, filed on Jan. 17, 2001, now Pat. No. 6,546,077.

(51) Int. Cl.
*B23K 28/00* (2006.01)

(52) U.S. Cl. .................................. 228/256; 228/121
(58) Field of Classification Search ................ 228/256, 228/121, 247, 253, 254, 262.72; 378/121, 378/136; 600/9; 445/28, 46
See application file for complete search history.

(56) References Cited

U.S. PATENT DOCUMENTS

| 2,531,583 | A |   | 11/1950 | Ott |
|---|---|---|---|---|
| 3,644,970 | A | * | 2/1972 | Seki et al. .............. 445/28 |
| 3,688,150 | A |   | 8/1972 | Wintzer |
| 4,901,904 | A | * | 2/1990 | Tsuno ..................... 228/56.3 |
| 5,012,102 | A |   | 4/1991 | Gowlett |
| 5,383,467 | A |   | 1/1995 | Auer et al. |
| 5,582,171 | A |   | 12/1996 | Chornenky et al. |
| 5,713,853 | A |   | 2/1998 | Clark et al. |
| 5,776,100 | A |   | 7/1998 | Forman |
| 5,854,822 | A |   | 12/1998 | Chornenky et al. |
| 5,860,584 | A | * | 1/1999 | Inazuru ................... 228/121 |
| 5,904,670 | A |   | 5/1999 | Schreiner |
| 5,925,016 | A |   | 7/1999 | Chornenky et al. |

(Continued)

OTHER PUBLICATIONS

Ward, R.W., "The Constants of Alpha Quartz," $14^{th}$ Piezo-electric Devices Conference and Exhibition, Sep. 15–17, 1992, Sponsored by Components Group EIA, 1992, (See especially Table I, pp. 3–4).
U.S. Appl. No. 08/701,764, filed Aug. 1996, Chornenky et al.
U.S. Appl. No. 09/806,244, filed Feb. 1997, Chornenky et al.

*Primary Examiner*—Jonathan Johnson

(57) ABSTRACT

An emitter for a miniature X-ray apparatus comprises an insulating shell, an anode, and a cathode. The insulating shell includes a conical brazing surface, brazed to a conical brazing surface on the anode. The braze consists of a pure titanium layer and a pure tin layer. During brazing, the pure metals react and bond to the insulating shell and create a titanium-tin alloy between the pure layers. Pure tin is sputtered from tin sputter target onto the exposed brazing surfaces of the cathode cap and the anode. The insulating shell is placed in a vacuum chamber of deposition applicator, which deposits an active metal onto the shell brazing surface. In a brazing oven, the anode is placed within insulating shell such that the anode conical brazing surface and the shell conical brazing surface are contacting and aligned with each other. During brazing, the cathode is brought into contact with the insulating shell. The sealed emitters are placed in a sputtering machine's vacuum chamber. A metal is sputtered from a sputtering target to form a metal layer on the exterior of insulating shell.

18 Claims, 6 Drawing Sheets

U.S. PATENT DOCUMENTS

| | | |
|---|---|---|
| 6,069,938 A | 5/2000 | Chornenky et al. |
| 6,095,966 A | 8/2000 | Chornenky et al. |
| 6,108,402 A | 8/2000 | Chornenky |
| 6,134,300 A | 10/2000 | Trebes et al. |
| 6,148,061 A | 11/2000 | Shefer et al. |
| 6,275,566 B1 | 8/2001 | Smith et al. |
| 6,415,016 B1 | 7/2002 | Chornenky et al. |
| 6,702,177 B1 * | 3/2004 | Totino et al. ............... 228/252 |
| 6,749,101 B1 * | 6/2004 | Lee et al. .................. 228/107 |
| 6,799,075 B1 * | 9/2004 | Chornenky et al. ......... 607/117 |

* cited by examiner

METHOD OF MANUFACTURING A MINIATURE X-RAY DEVICE

BACKGROUND OF THE INVENTION

1. Field of the Invention

The present invention relates generally to a miniature X-ray device. More specifically, the present invention relates to an X-ray catheter. More specifically, the present invention relates to an X-ray device having a braze joint between electrodes and insulating materials.

2. Background Art

Cardiovascular diseases affect millions of people, often causing heart attacks and death. One common aspect of many cardiovascular diseases is stenosis, or the thickening of an artery or vein wall, decreasing blood flow through the vessel. Angioplasty procedures have been developed to reopen clogged arteries without resorting to a bypass operation. However, in a large percentage of cases, arteries become occluded again after an angioplasty procedure. This recurrent thickening of the vessel wall is known as restenosis. Restenosis frequently requires a second angioplasty and eventual bypass surgery. Bypass surgery is very stressful on the patient, requiring the chest to be opened, and presents risks from infection, anesthesia, and heart failure.

One method of treating restenosis includes using miniature X-ray devices to irradiate blood vessels and other human body cavities. An X-ray catheter is comprised of a coaxial cable and a miniature X-ray emitter-connected to the cable's distal end. The proximal end of the coaxial cable is connected to a high voltage power source. The X-ray emitter consists of an anode and a cathode assembly mounted in a miniature shell (tube), made of an insulator with very high dielectric strength. Typically, the anode is comprised of platinum, tungsten, or another heavy metal.

To activate the emitter, high voltage is applied between electrodes. A high electric field is generated at the cathode surface and causes field emission of electrons. Emitted electrons are accelerated by the electric field and impinge on the anode. As the electrons strike the anode, X-ray energy is produced and radiated. The radiation occurs as high-speed electrons are slowed or stopped by passing near the positively charged nuclei of the anode material, or, as incoming electrons collide with the anode atoms and knock the electrons near the anode nuclei out of orbit and replacing the knocked out electrons with other electrons.

For adequate production of X-ray, a high voltage source supplies the catheter with voltage in the range of 15 to 30 kV and current in the range of 10 to 100 µA. For coronary applications, the outer diameter of an X-ray emitter must be as small as 1.00 to 1.25 mm. Thus, specific material properties and characteristics are desired for each element in the emitter.

A material used for the shell of an X-ray emitting catheter must possess a very high dielectric strength (120–200 kV/mm) combined with high electrical resistivity ($10^{15}$ Ohm-cm), gas impermeability, and moderate mechanical strength. A brazing process bonds the shell to the anode. In order to reliably join with the anode, the shell material should have a coefficient of thermal expansion (CTE) close to that of the anode and the braze layer that joins the anode and the shell. Finally, the shell material should have low to moderate absorption of X-ray within the energy range of 10–20 kV. Thus, the material should be composed of relatively low weight elements.

The shell must be hermetically sealed to the anode and cathode. Typically, this is done using a brazing process. The shell-to-cathode joint is relatively easy to obtain, and can employ a butt joint. The cathode is electrically connected to the metallic coating outside the shell, and there is no voltage applied to or through the joint.

However, the shell-to-anode joint is more difficult. The anode must be placed inside the shell and the joint should be able to withstand high voltage applied between the outer surface of the shell and the anode. The joint is typically exposed to an electric field of about 100 to 150 kV/mm. This strong electric field imposes several very strict requirements not only on the material itself, but also on the quality of the joint. For instance, any voids formed in the brazing layer enhance the electric field, which leads to dielectric breakdown. Additionally, any sharp points of braze or any spill of excess braze also enhances the electric field, again causing dielectric breakdown.

In order to avoid voids, points or spills, it is critical that the braze material not flow beyond the braze area. Brazing of emitters for catheter X-rays creates real limitations on the volume of materials that can be used in a braze joint. Thus, the quantity of material used in a braze joint must be carefully controlled. Conventionally, braze preforms are made and placed on the braze surfaces prior to the brazing process. However, because it is difficult to fabricate braze preforms having a thickness of 25 microns or less, the amount of braze material applied to the brazing joint typically exceeds the amount of braze material needed. Thus, overflow and spills are not uncommon when brazing catheter emitters. This leads to an increased electrical field during use and ultimately results in dielectric breakdown.

Furthermore, mass production of X-ray emitters using very small braze preforms is difficult to achieve because each braze preform must be individually placed on the brazing surfaces of the catheter emitters. This is a time consuming and difficult process.

Two types of brazing currently exist: metal brazing and nonmetal brazing. Metal brazing consists of placing a first easy-to-melt metal between two metals with higher melting points. The metals are heated until the low-melting point metal liquefies. While melted, the first metal bonds with the layers of the second metal, creating the braze. Upon cooling of the heated pieces, the pieces are inseparable, as they have been fused together.

The second type of brazing is for nonmetals. This type of brazing consists of brazing nonmetal materials, such as quartz or alumina, to a metal by adding an active metal, such as titanium or zirconium, to the braze material. The active metal is attracted to and reacts with the nonmetal, creating a chemical bond. This brazing process is referred to as active brazing. Active brazing usually requires high temperatures to liquify or dissolve the active metal to enable reaction between the active metal and the nonmetal. Quartz and alumina are examples of nonmetals that are brazed using active metals.

Thus, what is needed is a low temperature method of brazing that creates a strong chemical bond with a nonmetal surface. Further, what is needed is an easy way to manufacture batches of catheter X-ray emitters while carefully controlling the volume of braze material applied for a braze joint.

BRIEF SUMMARY OF THE INVENTION

This invention relates to an emitter for a miniature X-ray apparatus comprising an insulating shell, an anode, and a cathode and to a method of manufacturing such an emitter. The insulating shell includes a conical brazing surface, brazed to a conical brazing surface on the anode. The braze consists of a pure titanium layer and a pure tin layer. During brazing, the titanium dissolves and bonds to the shell, and forms a titanium-tin alloy layer.

The method of the invention includes placing anodes and cathodes into a vacuum chamber of a sputtering apparatus. Pure tin is sputtered from a tin sputtering target onto brazing surfaces.

The insulating shell is placed in a vacuum chamber of an arc ion deposition applicator, which emits a plasma stream of magnetically confined titanium plasma. The plasma adheres to the exposed shell brazing surface.

The insulating shell is placed in a vacuum chamber of a brazing oven. The anode is placed within the insulating shell such that the anode conical brazing surface and the insulating shell conical brazing surface are in contact and aligned with each other.

At the brazing temperature of 450–750° C., the cathode is brought into contact with the insulating shell. The oven temperature is slowly decreased to room temperature, and the sealed emitters are unloaded.

Finally, the sealed emitters are placed in a sputtering machine's vacuum chamber. A metal is sputtered from a sputtering target to form a metal layer on the exterior of insulating shell.

BRIEF DESCRIPTION OF THE DRAWINGS/FIGURES

The foregoing and other features and advantages of the invention will be apparent from the following, more particular description of a preferred embodiment of the invention, as illustrated in the accompanying drawings.

DETAILED DESCRIPTION OF THE INVENTION

The preferred embodiment of the present invention is now described with reference to the figures where like reference numbers indicate identical or functionally similar elements. While the invention is described in terms of a specific embodiment, it should be understood that this is done for illustrative purposes only. A person skilled in the relevant art will recognize that various modifications, rearrangements and substitutions can be made without departing from the spirit of the invention.

Figure 1:
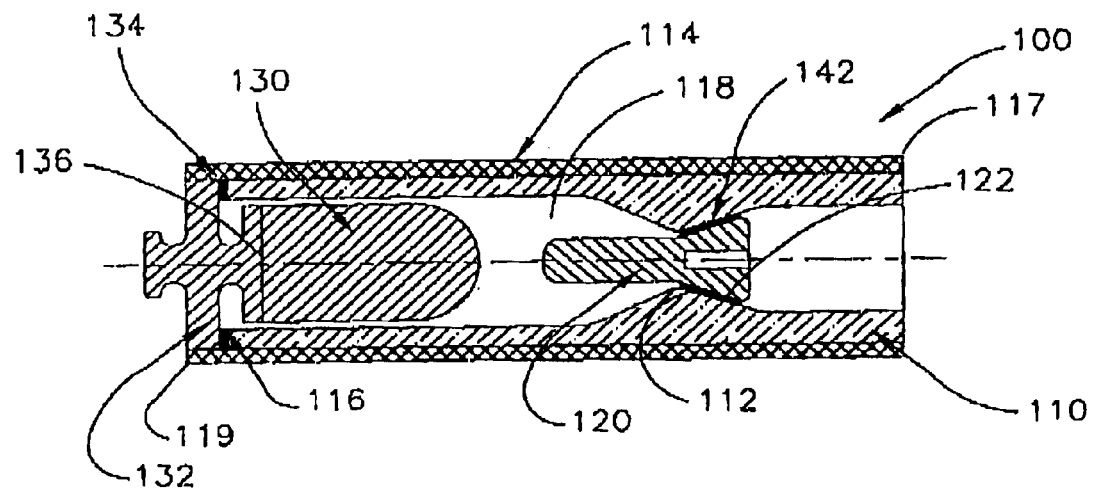
FIG. 1 shows an embodiment of a miniature X-ray emitter.

FIG. 1 shows a miniature a miniature X-ray emitter generally at 100. X-ray emitter 100 is to be introduced to a patient's blood vessels or other cavities via a trocar or introducer. It comprises a insulating shell 110, an anode 120, a cathode 130 and a cathode cap 132. Insulating shell has a first end 117 and a second end 119. Insulating shell 110 can be comprised of any material having a very high dielectric strength (120–200 kV/mm) combined with high electrical resistivity ($10^{15}$ Ohm-cm), gas impermeability, and moderate mechanical strength. Insulating shell 110 should also have a coefficient of thermal expansion (CTE) close to that of anode 120. Finally, insulating shell 110 should have low to moderate absorption of X-ray within the energy range of 10–20 kV. Thus, the material should be composed of relatively low weight elements. Crystalline quartz and diamond both meet these requirements, and are good materials for the insulating shell. The anode is preferably tungsten, however, platinum, gold or other heavy metals are also good materials for the anode.

Insulating shell 110 is coated with a metal coating 114, which provides electrical contact between cathode cap 132 and the braid of a coaxial cable (not shown). Metal coating 114 may be any non-corrosive conductive metal, as would be known by one skilled in the relevant art, and is preferably silver.

Outside the patient's body the cable is secured to a pullback device, which can be used to pull the cable to move the emitter along the blood vessel or the body cavity to provide irradiation for a predetermined length.

Cathode cap 132 is brazed or bonded to cathode 130 at cathode bond 136, using any method known to one skilled in the relevant art, and provides an electrical contact between cathode cap 132 and cathode 130.

Cathode cap 132 has a cap brazing surface 134 aligned to meet a shell brazing surface 116. Insulating shell 110 includes a conical brazing surface 112, brazed with a conical braze 142 to a conical anode brazing surface 122 on anode 120. The CTE of conical braze 142 should be close to that of anode 120 and insulating shell 110. Anode 120 is electrically connected to an interior wire of the coaxial cable, completing a circuit.

In use, cathode 130 is contained in an interior space 118 of insulating shell 110. Interior space 118 is kept at a vacuum environment. High voltage is applied through the braided portion of the coaxial cable to metal coating 114. The voltage is carried from metal coating 114 through the electrically connected cathode cap 132 to cathode 130. The applied voltage causes an electric field to generate around cathode 130, causing cathode 130 to emit electrons, which travel through the vacuum toward anode 120. As the electrons approach the anode, they are deflected by the positively charged nuclei of the anode material, losing energy and changing band frequency into X-ray band.

Conical braze 142 is subject to a very high electrical field between metal coating 114 on the outer surface of insulating shell 110 and anode 120. The electric field is typically around 100–150 kV/mm. Because of the high electric field, it is critical that conical braze 142 contain no voids or sharp points, which would enhance the electric field, and could lead to dielectric breakdown. Voids in a braze and spills that may create sharp points can be prevented by carefully controlling both the volume of the braze material and the space of the joint to be filled.

In a preferred embodiment, insulating shell 110 is crystalline quartz. The α→β transition temperature of quartz is 573° C. If quartz is heated and cooled through this transition temperature, a potentially destructive displasive transformation occurs. Thus, it is preferable that any brazing of crystalline quartz should be performed at temperatures close to or below this transition temperature. Additionally, this low brazing temperature helps keep generated thermal stresses at the braze joint to an acceptable level. However, due to CTE mismatches between dissimilar materials, thermal stresses are always present in a quartz-to-metal joint.

Brazing of crystalline quartz can also be successfully performed at temperatures higher than the transition temperature, up to 750° C. In this case, however, two conditions should be met to minimize destruction of the shell. First the quartz shell should be fabricated in such a way that the longitudinal axis of the shell is parallel with the crystallographic c-axis of quartz. The second condition is to cool down the assembly very slowly at the end of the brazing cycle, preferably at a rate of 1–5° C. per minute.

Figure 2:
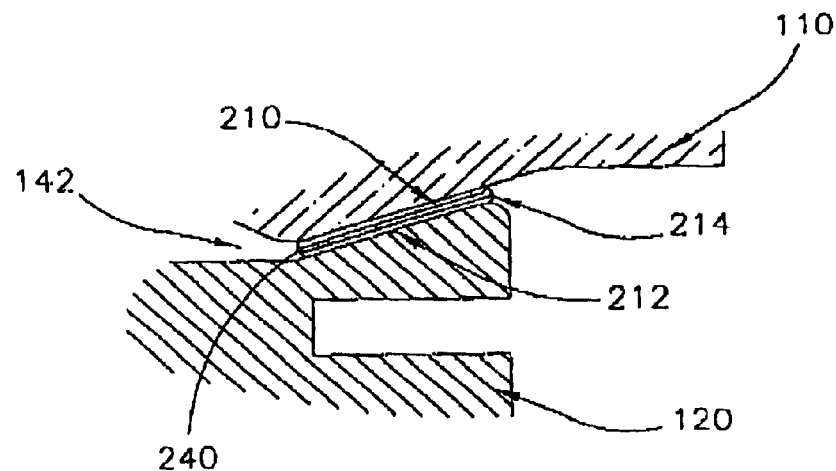
FIG. 2 shows a detailed sectional view of a conical braze area.

FIG. 2 shows a close up view of the area of conical braze 142 in detail. Insulating shell 110, consisting of crystalline quartz (in this embodiment), has attached to it a pure titanium layer 210. Anode 120 has attached to it, a pure tin layer 212. Between titanium layer 210 and tin layer 212 is a titanium-tin alloy layer 214.

It is important when creating the conical braze 142 to ensure that there are no voids, spills or sharp points in the braze that might enhance the electrical energy field and cause dielectric breakdown. The method of the present invention allows such sharp points and spills to be avoided by providing a lip or meniscus 240 having a rounded edge (described below). The method of performing the braze, as well as the unique properties of the braze will be explained in detail below, with reference to FIGS. 3–6.

Figure 3:
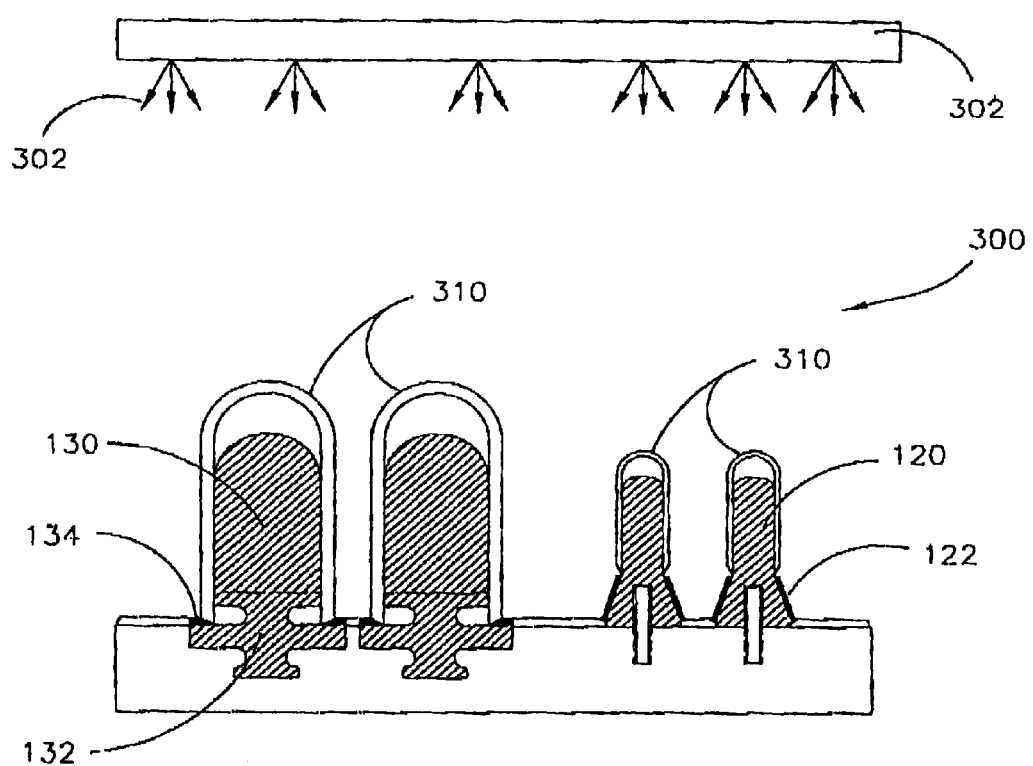
FIG. 3 shows a sputtering apparatus in use with the invention.

FIG. 3 shows an embodiment of a sputtering apparatus 300. Sputtering apparatus 300 could be any sputtering apparatus known in the relevant art. In one embodiment, sputtering apparatus 300 is a planar magneton sputtering unit from Anatech Ltd., Springfield, Va. Prior to using sputtering apparatus 300, cathode 130 and cathode cap 132 are brazed together using standard brazing methods known to one skilled in the relevant art.

Anodes 120 and cathodes 130, along with cathode caps 132, are placed in a vacuum chamber of sputtering apparatus 300. Masks 310 are appropriately placed over both anodes 120 and cathodes 130, with cathode caps 132, leaving only the cathode cap brazing surface 134 and the conical anode brazing surface 122 exposed. Pure tin 312 is sputtered from tin sputter target 302 onto the exposed cathode cap brazing surface 134 and the anode brazing surface 122. Other surfaces of anode 120 and cathode 130 are properly covered, so that tin 312 cannot adhere to those surfaces.

It is important that only a proper amount of tin be sputtered onto the brazing surface to prevent overflow or running of the tin. As stated above, excess material will enhance the electric field generated during use and could result in dielectric breakdown. The proper amount of tin is found by calculating the volume of the space to be filled by the braze material, and subtracting the volume to be filled by the titanium, as would be apparent to one skilled in the relevant art. The volume is the sum of the volume of the manufacturing tolerances and the surface roughness. In this embodiment, tin is applied on the exposed cap brazing surface 134 and the conical anode brazing surface 122 until a tin layer having a thickness of about 20–50 micrometers is achieved.

Upon sputtering the desired layer thickness of tin on cathode cap brazing surface 134 and conical anode brazing surface 122, anode 120 and cathode 130, along with cathode cap 132, are removed from the sputtering apparatus.

Although only two cathodes and two anodes are shown in FIG. 3, there could be up to hundreds of cathodes and anodes placed in the vacuum chamber for simultaneous processing.

Figure 4:
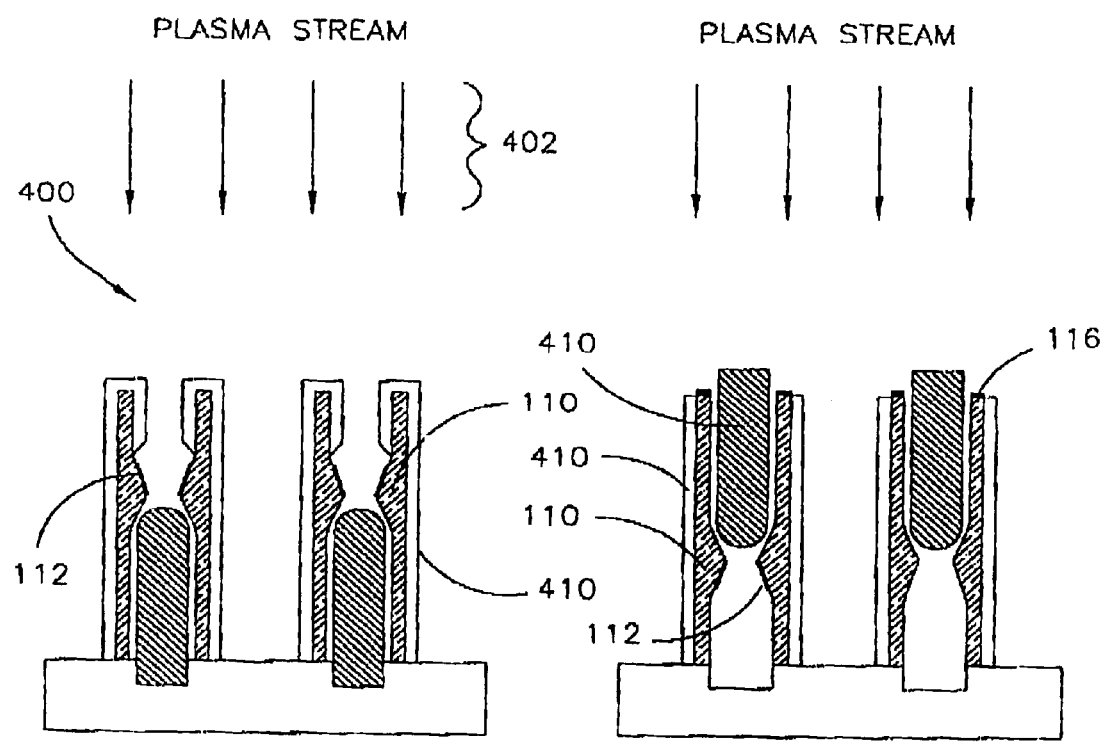
FIG. 4 shows a cathodic arc deposition applicator in use with the invention.

FIG. 4 shows an embodiment of a titanium applicator 400. Applicator 400 could be any high energy deposition apparatus, as would be apparent to one skilled in the relevant art. One example of a high energy deposition apparatus suitable for carrying out the invention is a cathodic arc ion plating apparatus such as Focused Cathodic Arc Source, FCA100 from ISM Technologies, Poway, Calif.

According to the invention, insulating shell 110 is placed in a vacuum chamber of apparatus 400. Insulating shell 110 is covered with a mask 410, leaving only shell conical brazing surface 112 and shell brazing surface 116 exposed, depending on the configuration, as can be seen in FIG. 4. In the embodiment shown, only one of shell conical brazing surface 112 and shell brazing surface 116 are exposed at a given time. However, as would be apparent to one skilled in the relevant art, either end could first be exposed, followed by the remaining end, or both ends exposed at the same time.

An applicator (not shown) emits magnetically confined titanium plasma 402. The plasma adheres to the exposed shell brazing surface 116 and shell conical brazing surface 112. The titanium plasma has ion energy of about 75 eV. Thus, the plasma is good for adhesion and for reaching regions deep inside apertures with high aspect ratios. Plasma has the unique characteristic of flowability. Plasma, like a gas, can penetrate areas where a typical sputterer cannot. Conventional sputtering techniques are unable to provide high bonding energy and deposition in such regions. This is because conventional sputtering techniques include emitting particles that travel in a straight line, although they are emitted in all directions. Thus, with conventional sputtering techniques, as the aspect ratio of a tubular component increases, the chance that any single particle will travel deep into the tubular component, rather than contacting an interior sidewall, decreases. However, flowability allows titanium plasma to reach into the interior surfaces of insulating shell to coat shell conical brazing surface 112.

Additionally, the conical profile of shell conical brazing surface 112 allows deposition to easily settle on a surface. Because conical surface 112 extends from the cylindrical interior of insulating shell 110, plasma 402 can reach the surface and deposit titanium on the conical surface. Thus, plasma deposition is very efficient and useful for depositing particles in high aspect ratio holes, significantly decreasing the length of time required to obtain a sufficient coating. Furthermore, the flowability of plasma allows corners to be coated with plasma without difficulty.

Although other metals could be used, as would be apparent to one skilled in the relevant art, titanium is preferred, as it is an active metal, which allows strong bonds between an applied titanium film and a non-metallic substrate, such as quartz insulating shell 110.

It is important to control the amount and the area of titanium placed on shell conical brazing surface 112 and shell brazing surface 116. An excess of braze material could result in overflow and development of sharp points that would increase the electric field during use and possibly cause dielectric failure. Again, the amount of material necessary to fill the area between insulating shell 110 and anode 120 will be calculated to fill the volume of the area between insulating shell 110 and anode 120. Preferably, the thickness of the titanium layer is about 3–7 microns thick.

FIG. 4 shows a total of four insulating shells 110 in titanium applicator 400. However, as would be apparent to one skilled in the relevant art, a batch of up to several hundred insulating shells 110 could be processed simultaneously.

Figure 5:
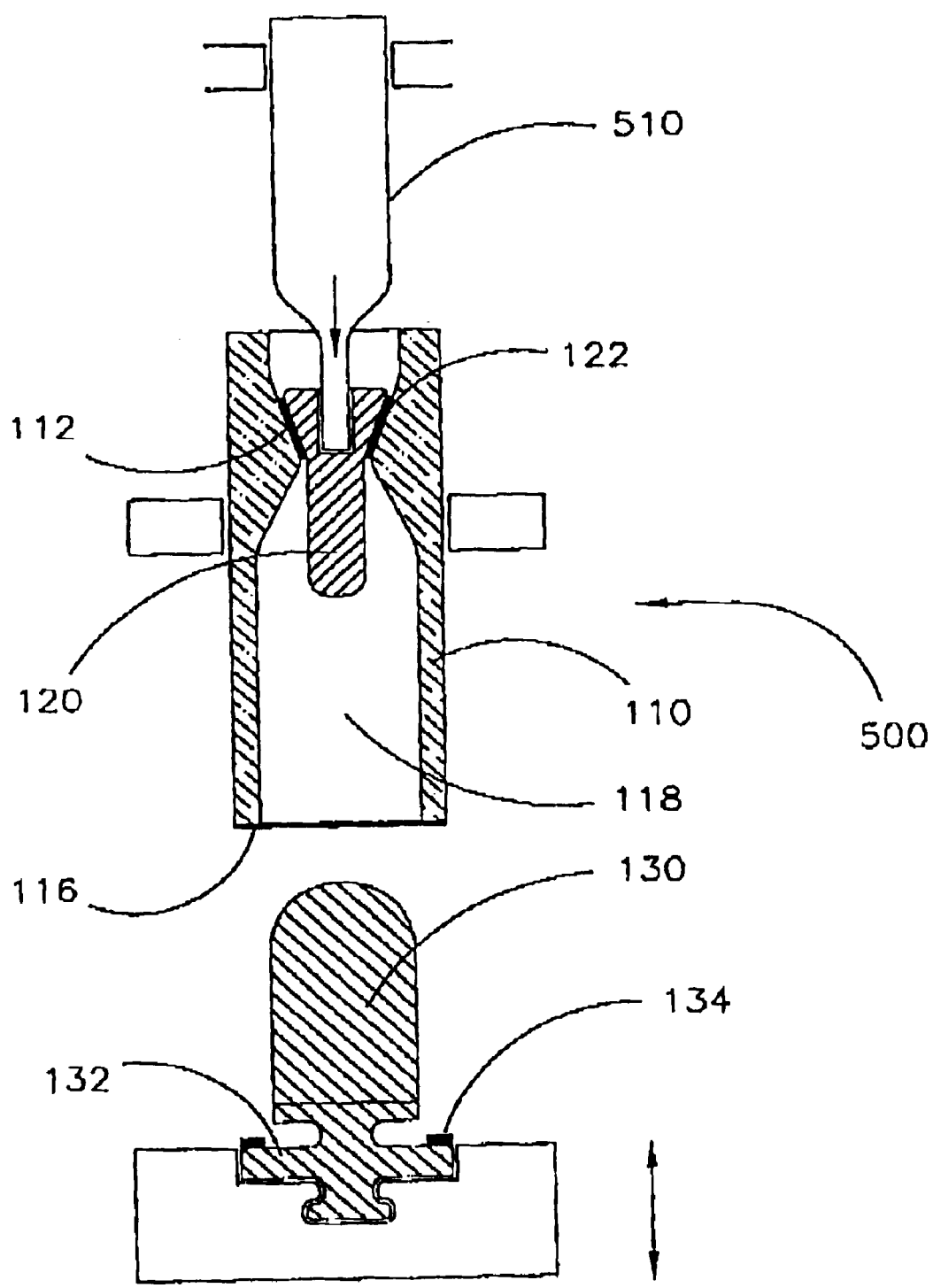
FIG. 5 shows the assembly and brazing and sealing procedure of the emitter.

FIG. 5 depicts the procedure of sealing anode 120 and cathode 130 into insulating shell 110. Insulating shell 110 is placed in a vertical position in vacuum chamber of a brazing oven. Anode 120 is placed within insulating shell 110, such that the conical anode brazing surface 122 and the shell conical brazing surface 112 are aligned and mated with each other. By so doing, tin layer 212 is in contact with titanium layer 210. A small axial load on anode 120 causes the tin layer and the titanium layer to firmly engage, and, due to the conical configuration, causes anode 120 to center itself within insulating shell 110. The axial load can be either the weight of anode 120 or an applied load, as would be apparent to one skilled in the relevant art. In the embodiment shown, the axial load is applied by a plunger 510. Cathode 130, previously bonded, sealed or brazed to cathode cap 132 by methods known to those in the relevant art, is place directly below insulating shell 110, at some distance to enable a flow of gases out from interior space 116 of insulating shell 110 during the heating and vacuum phase.

After loading the pieces, the brazing oven is vacuumed to $10^6$ Torr and is step heated to 150–200° C. The oven temperature is increased to 450–550° C. at a rate of 15–30° C./min., and held for 0–10 minutes. During this heating step, the pure tin liquifies and all the gaseous species in the oven will outgas. This heating step activates low-temperature getters, placed as a part of cathode 130 prior to sealing. This, at the same time, allows the getters to pump interior space 118 to obtain the desired vacuum level and maintain the vacuum in interior space 118 long after long after the manufacturing process. Low temperature getter material could be comprised of zirconium-vanadium-iron such as could be procured from SAES Getters, as would be apparent to one skilled in the relevant art.

In one embodiment, getter material is incorporated into the material of cathode 130, such that cathode 130 directly absorbs gas molecules from the interior space.

After holding the brazing oven temperature at 450–550° C. for the time necessary to activate the getters and pump interior space 118, the oven temperature is further increased to the brazing temperature at a rate of 10–20° C. per minute, and held from 0–10 minutes. During this heating step, the titanium-tin reaction occurs, thus brazing anode 120 to insulating shell 110. The oven temperature is very slowly decreased to 500–550° C., preferably at a rate of 1–5° C. per minute. This controlled slow cooling is critical when crystalline quartz is brazed at temperatures higher than the α→β transition temperature. The oven temperature is further decreased to room temperature at a rate of 15–25° C. per minute, and the sealed emitters 100 are unloaded.

To ensure out gassing all the gaseous species that might have been absorbed on the surface of the components, cathode cap brazing surface 134 can be separated from insulating shell 110 at temperatures between 200 and 300° C. for a short period of time, preferably less than 10 minutes. Cathode cap brazing surface 134 is then brought into contact by mechanical manipulation, under light compression, with insulating shell 110, and the oven temperature is increased to the brazing temperature as described above. Brazing ovens, capable of performing mechanical manipulations of parts in a vacuum can be procured from Scientific Sealing Technology, Inc., in Los Angeles, Calif.

Figure 7:
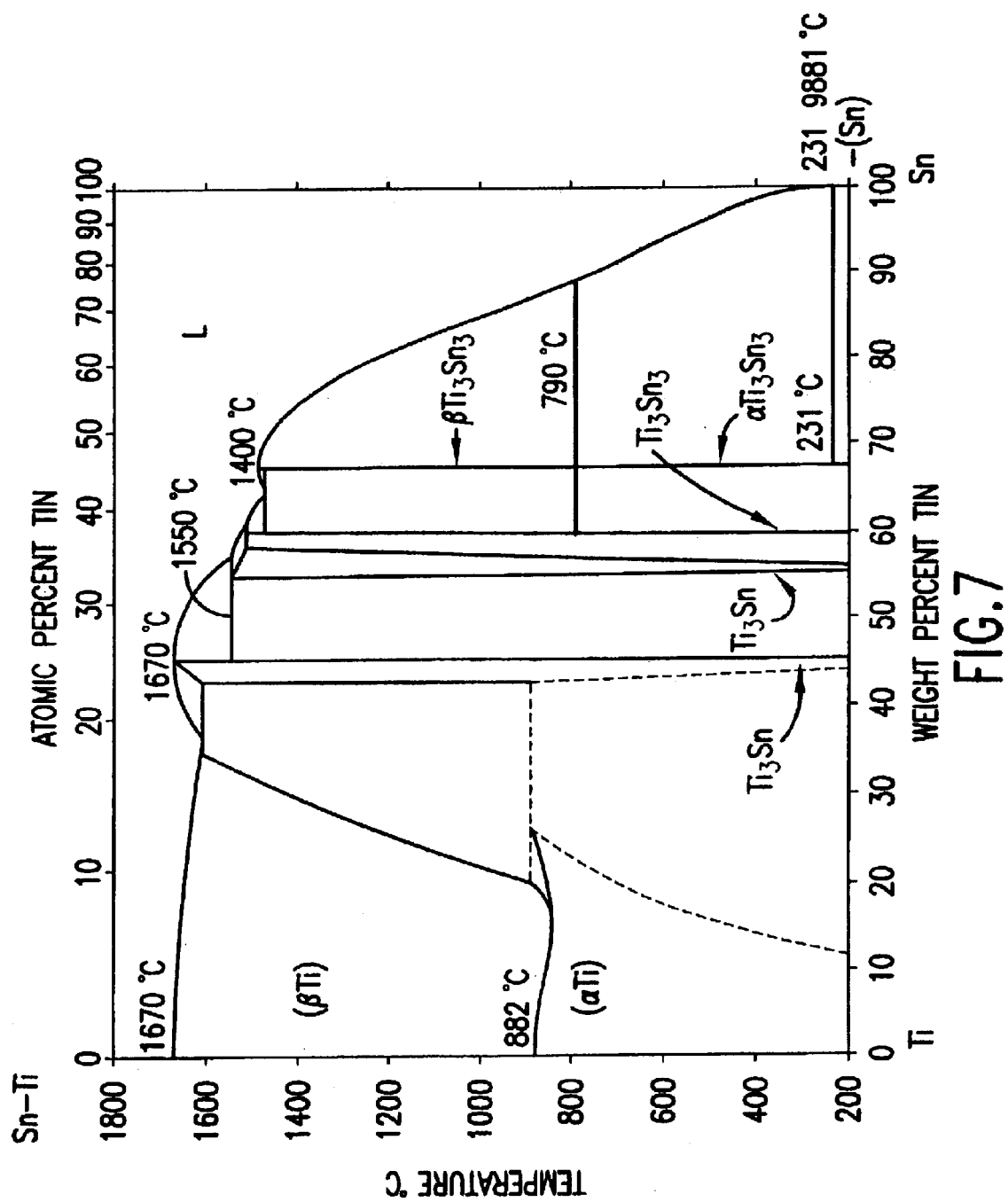
FIG. 7 shows a Ti—Sn binary phase diagram.

FIG. 7 shows a Ti—Sn binary phase diagram. As seen in FIG. 7, the melting temperature of pure tin is 232° C., while the melting temperature of pure titanium is 1670° C. Thus, in order to braze using titanium and tin, temperatures must be above the melting temperature of at least one metal, or, in this case, the melting temperature of tin. As tin melts, it begins to immediately dissolve solid titanium and create Ti—Sn alloys. As shown in FIG. 7, the amount of titanium dissolved into the molten tin is determined and limited by the location of the liquidus at a brazing temperature.

At the brazing temperature, as more titanium dissolves into the molten tin, the average composition of the whole liquid shifts toward the titanium-rich side and thus the melting point of the liquid increases.

As the melting point of the alloy increases, the Ti—Sn alloy will go through an isothermal solidification process. This unique alloy design allows the braze process to occur at any temperature between the melting point of tin (232° C.) up to the melting point of the Ti—Sn intermetallic (1400° C.). The amount of titanium dissolved by the tin is controlled by the applied temperature.

The sealing is performed at temperatures between 500° C. and 750° C., preferably at temperatures between 500 and 600° C. This low temperature braze allows bonding below 573° C., which is the α→β phase transition temperature of quartz. The brazing temperature is also above the minimum activation temperature for the getter, which is about 300° C. Finally, this brazing temperature is above the minimum temperature necessary for out gassing of the inside surfaces of the emitter, which is 400–450° C.

Figure 6:
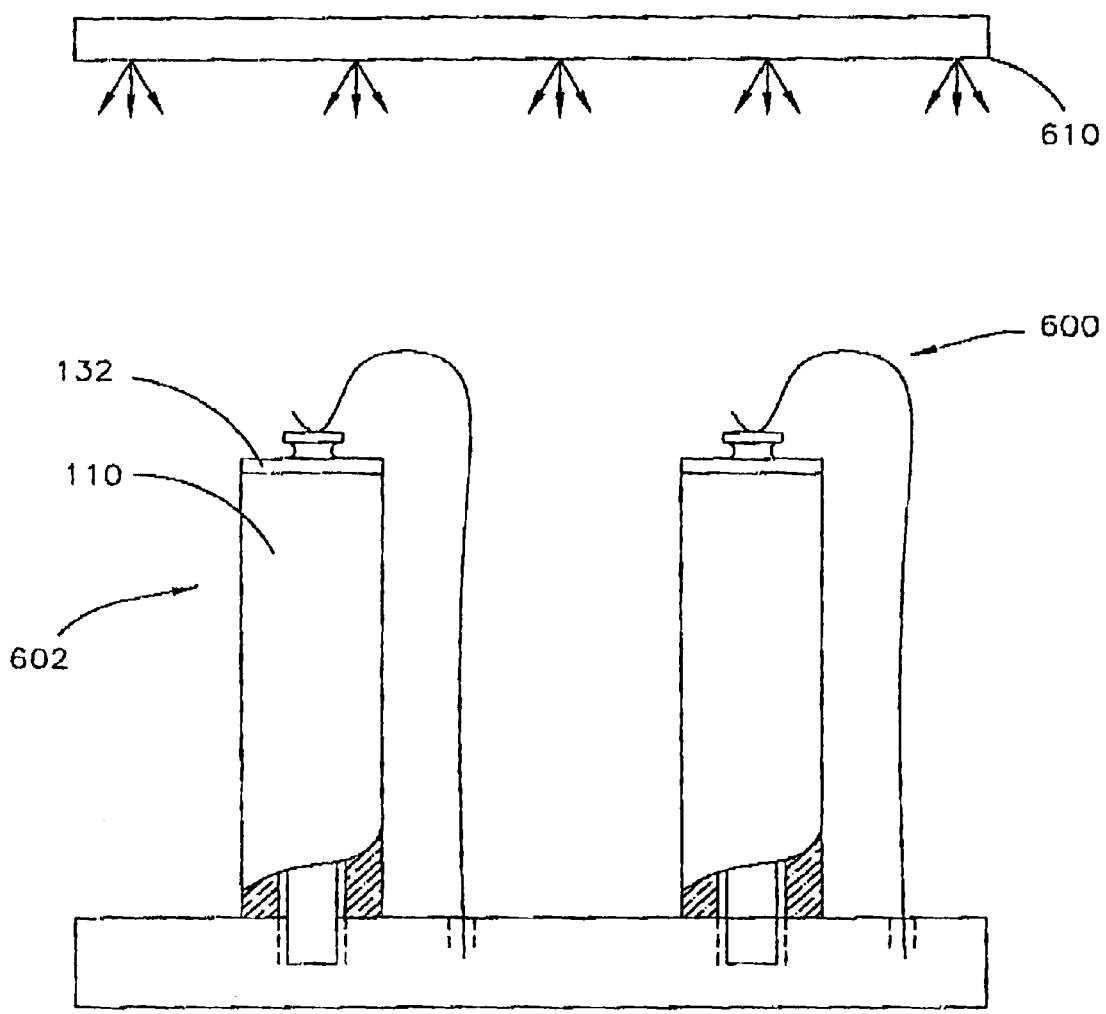
FIG. 6 shows a metal being sputtered onto the exterior surface of the emitter.

FIG. 6 shows the metallization of the outer surface of emitter 100. A batch of sealed emitters 602 is placed in a sputtering machine's vacuum chamber 600. Cathode caps 132 face a sputtering target 610. A metal, preferably silver, is sputtered from sputtering target 610 to form a metal layer on the exterior of cathode cap 132 and insulating shell 110. Other metals could be used as would be apparent to one skilled in the relevant art. In a preferred embodiment, the metal is sputtered onto emitter 602 to provide a 1–5 micron thick layer of metal, however, the layer could be more or less thick, as would be apparent to one skilled in the relevant art.

The metal layer 114 on the outer surface of emitter 602 performs several important functions: it provides a return path for the operating current, electrical safety for the patient, shields the triple point of the emitter thereby increasing its hold off voltage, and focuses the electron beam along the axis of the emitter, preventing charging the inside wall of the insulating shell and discharges associated with it. Finally, the completed coated emitter is removed from vacuum chamber 600.

One advantage of the present invention is that it provides for batch processing of catheter X-ray emitters. Large batches, preferably about 500, can be simultaneously sputtered, deposited and brazed, saving time and lowering costs.

Another advantage is that the sputtering and deposition of the pure metals allows ultra-fine control of the amount of material used for the braze. Thus, the chance of overflow or running is virtually eliminated. Additionally, the brazing can be performed at low temperatures, allowing dielectrics such as crystalline quartz to remain below the α->β transition temperature. Even when the brazing is performed at temperatures higher than the α->β transition temperature, up to 750° C., destructive failure of the shell can be avoided by precisely controlling the heating/cooling steps as described above.

Additionally, the present invention assists in reducing the chance of dielectric failure by reducing the chance of voids, points or spills of braze material. The method provides an easily controlled braze area without chance of additional running or spilling of braze material onto the surface of insulating shell 110. Additionally, as seen in FIG. 2, conical braze 142 comprises a meniscus 240 having a rounded edge.

High energy plasma deposition, along with the use of masks 410, allows complete control of the placement and quantity of titanium applied to shell 110. A dividing line, or stopper, is created at the line dividing the coated material from the uncoated material. Because the brazing temperature remains far below the melting temperature of pure titanium (1670° C.) the pure titanium deposited on shell conical brazing surface 112 will not flow or change position. This stopper line also eliminates flow of melted braze material from the braze area onto the shell region not coated with titanium. The tin alone cannot react with quartz, and thus will not wet or flow onto the uncoated quartz region. However, it will flow around the corner of the deposited titanium to completely envelope deposited titanium coating. This creates a round edge or a meniscus. Meniscus 240 eliminates edges or points that may enhance the electric field, and allows the braze to withstand the high voltage required for X-ray emission and electric field generations. Such a brazed joint can withstand up to 1 million V/cm.

While the invention has been particularly shown and described with reference to preferred embodiments thereof, it will be understood by those skilled in the art that various changes in form and detail may be made therein without departing from the spirit and scope of the invention.

What is claimed is:

1. A method for brazing a nonmetal material, comprising:
   applying a pure tin layer onto a brazing surface of a first material;
   applying a pure titanium layer onto a brazing surface of a second material;
   aligning said brazing surface of said first material with said brazing surface of said second material, such that said tin layer and said titanium layer are in contact; and
   heating said tin layer and said titanium layer, wherein said tin layer liquifies and bonds with at least a portion of said titanium layer.

2. The method of claim 1, wherein said tin layer is applied by sputtenng.

3. The method of claim 1, wherein said titanium layer is applied by cathodic arc ion deposition.

4. The method of claim 3, wherein said titanium layer is 3–7 microns thick.

5. The method of claim 1, wherein said heating is performed in a vacuum environment of $10^{-6}$ torr.

6. The method of claim 1, wherein said heating step activates getters.

7. The method of claim 1, wherein said bonding occurs between temperatures of 500–7500° C.

8. The method of claim 1, further comprising applying a metal coating onto the outer surface of the shell.

9. The method of claim 8, wherein said metal is silver and is 1–5 micron thick.

10. A method for brazing an emitter for delivery of X-ray radiation, comprising:
    applying by sputtering a first metal onto a conical surface of an anode;
    applying a second metal onto a conical surface of an insulating shell, wherein said insulating shell has first end and a second end;
    thermally bonding said first metal on said conical area of said anode into said insulating shell, directly to said second metal on said conical area of said insulating shell; and
    bonding a cathode within the second end of said insulating shell.

11. The method of claim 10, wherein said second metal is applied by cathodic arc deposition.

12. The method of claim 10, wherein said first metal is tin and said second metal is titanium.

13. The method of claim 12, wherein said titanium is 3–7 microns thick.

14. The method of claim 10, further comprising, placing said anode, said cathode, and said insulating shell into a brazing oven and vacuuming to $10^{-6}$ torr.

15. The method of claim 14, wherein the oven is heated to activate getters.

16. The method of claim 14, wherein said thermal bonding occurs between temperatures of 500 and 750° C.

17. The method of claim 10, further comprising applying a metal onto the outer surface of said shell.

18. The method of claim 17, wherein said metal is silver and is 1–5 microns thick.

* * * * *

UNITED STATES PATENT AND TRADEMARK OFFICE
CERTIFICATE OF CORRECTION

PATENT NO. : 7,086,577 B2 Page 1 of 1
APPLICATION NO. : 10/358265
DATED : August 8, 2006
INVENTOR(S) : Victor I. Chornenky et al.

It is certified that error appears in the above-identified patent and that said Letters Patent is hereby corrected as shown below:

Column 9, line 41, "by sputtenng." should be changed to --by sputtering. --

Signed and Sealed this

Twenty-third Day of October, 2007

JON W. DUDAS
*Director of the United States Patent and Trademark Office*